United States Patent
Van Der Waal et al.

(10) Patent No.: US 11,059,768 B2
(45) Date of Patent: Jul. 13, 2021

(54) CONTINUOUS OR SEMI-CONTINUOUS PROCESS FOR THE PREPARATION OF ETHYLENE GLYCOL AND CATALYST SYSTEM FOR USE THEREIN

(71) Applicant: Avantium Knowledge Centre B.V., Amsterdam (NL)

(72) Inventors: Jan Cornelis Van Der Waal, Amsterdam (NL); Paula Dekker, Amsterdam (NL); Jagdeep Singh, Amsterdam (NL); Benjamin McKay, Amsterdam (NL)

(73) Assignee: Avantium Knowledge Centre B.V., Amsterdam (NL)

( * ) Notice: Subject to any disclaimer, the term of this patent is extended or adjusted under 35 U.S.C. 154(b) by 0 days.

(21) Appl. No.: 16/977,740

(22) PCT Filed: Mar. 14, 2019

(86) PCT No.: PCT/EP2019/056509
§ 371 (c)(1),
(2) Date: Sep. 2, 2020

(87) PCT Pub. No.: WO2019/175362
PCT Pub. Date: Sep. 19, 2019

(65) Prior Publication Data
US 2021/0002192 A1    Jan. 7, 2021

(30) Foreign Application Priority Data
Mar. 14, 2018 (NL) .................................. 2020584

(51) Int. Cl.
| | | |
|---|---|---|
| *C07C 29/132* | (2006.01) | |
| *B01J 19/00* | (2006.01) | |
| *B01J 19/24* | (2006.01) | |
| *B01J 23/30* | (2006.01) | |
| *B01J 23/46* | (2006.01) | |
| *C07C 31/20* | (2006.01) | |

(52) U.S. Cl.
CPC ......... *C07C 29/132* (2013.01); *B01J 19/0013* (2013.01); *B01J 19/24* (2013.01); *B01J 23/30* (2013.01); *B01J 23/462* (2013.01); *B01J 2219/00033* (2013.01); *C07C 31/202* (2013.01)

(58) Field of Classification Search
CPC .. C07C 29/132; C07C 31/202; B01J 19/0013; B01J 19/24; B01J 23/30; B01J 23/462; B01J 2219/00033; B01J 31/202
See application file for complete search history.

(56) References Cited

U.S. PATENT DOCUMENTS

2011/0313210 A1    12/2011    Kalnes et al.

FOREIGN PATENT DOCUMENTS

| CN | 102643165 B | 7/2014 |
|---|---|---|
| WO | 2016114660 A1 | 7/2016 |
| WO | 2016114661 A1 | 7/2016 |
| WO | 2017055289 A1 | 4/2017 |

OTHER PUBLICATIONS

International Search Report and Written Opinion dated Jun. 14, 2019 for PCT/EP2019/056509.
Written Opinion of the International Preliminary Examining Authority dated Feb. 24, 2020 for PCT/EP2019/056509.
International Preliminary Report on Patentability dated Apr. 16, 2020 for PCT/EP2019/056509.

*Primary Examiner* — Jafar F Parsa
(74) *Attorney, Agent, or Firm* — Suiter Swantz pc llo

(57) ABSTRACT

A continuous or semi-continuous process for the preparation of ethylene glycol from a carbohydrate source including: reacting, in a reactor, at a temperature in the range from equal to or more than 170° C. to equal to or less than 270° C., at least a portion of a carbohydrate source in the presence of hydrogen, a solvent, and a catalyst system, to yield ethylene glycol;
wherein the catalyst system includes:
a homogeneous catalyst, which homogeneous catalyst contains tungsten; and
a heterogeneous catalyst, which heterogeneous catalyst contains one or more transition metals from groups 8, 9 and 10 of the Periodic Table of the Elements supported on a carrier; and
wherein continuously or periodically additional heterogeneous catalyst is added to the reactor.
Further described is a catalyst system that can be used in such a process.

7 Claims, 1 Drawing Sheet

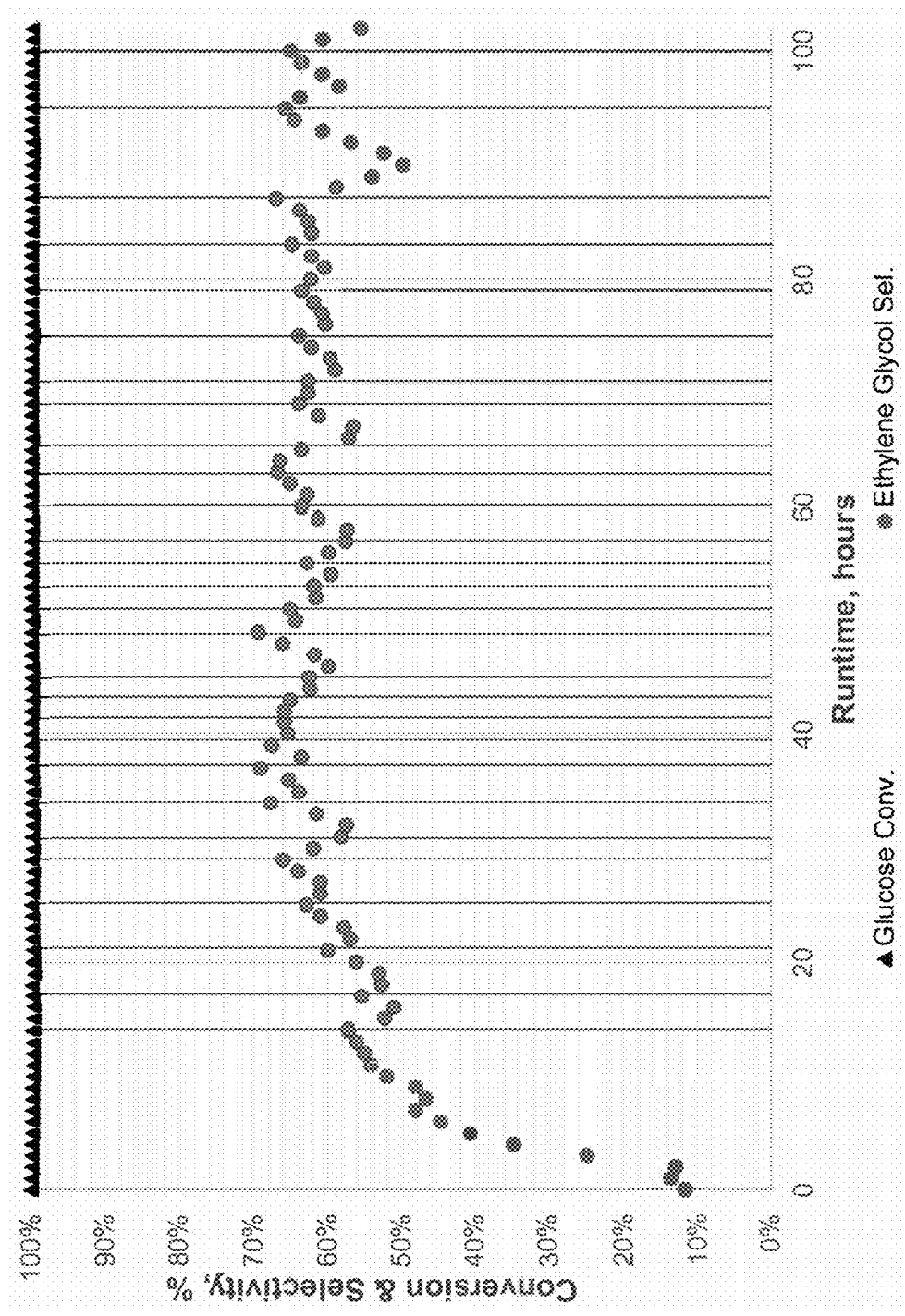

CONTINUOUS OR SEMI-CONTINUOUS PROCESS FOR THE PREPARATION OF ETHYLENE GLYCOL AND CATALYST SYSTEM FOR USE THEREIN

FIELD OF THE INVENTION

The present invention relates to a process for the production of ethylene glycol. The present invention further relates to a heterogeneous catalyst composition.

BACKGROUND TO THE INVENTION

Alkylene glycols, such as ethylene glycol, are bulk chemicals that can be used in a wide variety of applications. They can be used as monomer in the preparation of polyesters, such as poly(ethylene terephthalate), poly(ethylene naphthenate) or poly(ethylene furandicarboxylate), but ethylene glycol can also be used for example in heat transfer media and anti-freeze compositions.

Recently, increased efforts are being made to produce alkylene glycols from sustainable resources, such as carbohydrates. By enabling the preparation of alkylene glycols, such as ethylene glycol, from sustainable resources, the dependence of fossil fuel resources is advantageously reduced.

Y. Liu et al, in their article titled "Kinetic insight into the effect of the catalytic functions on selective conversion of cellulose to polyols on carbon-supported WO3 and Ru catalysts", published in Catalysis Today, vol. 269 (2016), pages 74 to 81, explain that the efficient conversion of carbohydrates to chemicals in high yields remains a formidable challenge. The distribution of products is said to depend on competitive reactions of glucose intermediates. WO3 crystallites are indicated not only to promote the hydrolysis of cellulose to glucose, but also to catalyze the selective cleavage of C—C bonds in glucose to form glycolaldehyde and in fructose to form glyceraldehyde. The Ru/C catalyzed hydrogenation of such glycolaldehyde to ethylene glycol and such glyceraldehyde to propylene glycol is indicated to be in competition with the Ru/C catalyzed hydrogenation of the glucose and fructose to corresponding C6-polyols such as sorbitol and mannitol. CN 102643165 B (in machine translation) discloses a continuous reaction process for catalyzing the hydrocracking of sugars to produce ethylene glycol and 1,2 propylene glycol in a reactor. The soluble catalyst components are partially recycled back to the reactor. US 2011/313210 relates to a catalytic process for generating at least one polyol from a feedstock comprising cellulose is performed in a continuous manner. The process involves, contacting, continuously, hydrogen, water, and a feedstock comprising cellulose, with a catalyst to generate an effluent stream comprising at least one polyol, water, hydrogen, and at least one co-product. The water, hydrogen, and at least one co-product are separated from the effluent stream and recycled to the reaction zone. The polyol is recovered from the effluent stream. The process may further comprise separating catalyst from the effluent stream and recycling the catalyst to the reaction zone. WO 2017/055289 discloses a process for the preparation of glycols from a saccharide-containing feedstock using a catalyst component with retro-aldol catalytic capabilities and a first hydrogenation catalyst comprising an element selected from groups 8, 9 and 10 of the periodic table. The process may further comprise separating catalyst from the effluent stream and recycling the catalyst to the reaction zone.

WO2016/114661 describes a continuous process for preparing ethylene glycol from a carbohydrate source by reaction of the carbohydrate source with hydrogen. In the process hydrogen, the carbohydrate source and a liquid diluent are continuously fed into a continuous stirred tank reactor (CSTR) wherein a catalyst system is present. The described catalyst system comprises a tungsten compound and at least one hydrogenolysis metal selected from the groups 8, 9 or 10 of the Periodic Table of the Elements. WO2016/114661 describes that continuously a product mixture comprising ethylene glycol and diluent is removed from the continuous stirred tank reactor; and further continuously or periodically at least a tungsten compound is added to the continuous stirred tank reactor. WO2016/114661 further explains that if and to the extent that any hydrogenolysis catalyst is removed from the CSTR during the reaction, such maybe complemented by periodical or continuous addition thereof to the CSTR.

In its examples WO2016/114661 illustrates interesting results with selectivity's towards ethylene glycol as high as about 60 wt. %, calculated as the weight percentage in the reactor effluent divided by the amount of grams glucose being introduced into the CSTR. The runtime in the experiments, however, did not exceed 7 hours. WO2016/114661 mentions that humins are formed which accelerate the deactivation of the catalyst and that accordingly the glucose conversion is decreased over time.

It would be an advancement in the art to provide a process for the preparation of ethylene glycol from a carbohydrate source, that would allow for a prolonged runtime with an economically interesting selectivity towards ethylene glycol.

SUMMARY OF THE INVENTION

Such a process has been obtained with the process according to the invention. Accordingly the present invention provides a continuous or semi-continuous process for the preparation of ethylene glycol from a carbohydrate source including:
reacting, in a reactor, at a temperature in the range from equal to or more than 170° C. to equal to or less than 270° C., at least a portion of a carbohydrate source in the presence of hydrogen, a solvent, and a catalyst system, to yield ethylene glycol;
wherein the catalyst system includes:
a homogeneous catalyst, which homogeneous catalyst contains tungsten; and
a heterogeneous catalyst, which heterogeneous catalyst contains one or more transition metals from groups 8, 9 and 10 of the Periodic Table of the Elements supported on a carrier; and
wherein continuously or periodically additional heterogeneous catalyst is added to the reactor.

The continuous or periodical addition of heterogeneous catalyst allows one to maintain the ethylene glycol selectivity.

The invention further provides a catalyst system including:
a) a homogeneous catalyst, that is preferably residing in a reactor, which homogeneous catalyst contains tungsten;
b) a first heterogeneous catalyst, that is preferably residing in the reactor, which first heterogeneous catalyst contains one or more transition metals from groups 8, 9 and 10 of the Periodic Table of the Elements supported on a carrier, and which first heterogeneous catalyst further contains an amount of tungsten; and c) a second heterogeneous catalyst, that is preferably continuously or periodically added to the reactor, which second heterogeneous catalyst contains one or more transition metals from groups 8, 9 and 10 of the Periodic Table of the Elements supported on a carrier, and which second heterogeneous catalyst contains no tungsten; or an amount of tungsten in a molar ratio of moles tungsten to moles transition metal that is less than the molar ratio of moles tungsten to moles transition metal of the first heterogeneous catalyst.

The inventors have now surprising found that the claimed process, respectively the claimed catalyst system, advantageously allows one to operate a process for the preparation of ethylene glycol from a carbohydrate source for a prolonged period of time with an economically interesting selectivity towards ethylene glycol. The process according to the invention may advantageously have a runtime of equal to or more than 50 hours and even equal to or more than 100 hours.

Aiqin Wang et al., in their article titled "One-Pot Conversion of cellulose to Ethylene Glycol with Multifunctional Tungsten-Based Catalysts" published in Accounts of Chemical Research (2013), vol. 46, pages 1377 to 1386, describe a one-pot catalytic conversion of cellulose to ethylene glycol. Aiqin Wang et al. suggest that when using tungsten compounds in combination with a hydrogenation catalyst such as Ni and Ru, dissolved $H_xWO_3$ is the genuinely catalytically active species for C—C cleavage, and the reaction for C—C cleavage of cellulose proceeds through a homogeneous catalysis pathway.

WO2016/114661 mentioned the believe that in the reducing atmosphere that is created in the reaction zone by means of the presence of hydrogen and carbohydrates, hexavalent tungsten compounds may be reduced to pentavalent tungsten and that in this partly reduced state the tungsten ions are effective in attacking the carbon-carbon bonds in the carbohydrate source to form alkylene glycol precursors.

Without wishing to be bound to any kind of theory, inventors believe that the heterogeneous catalyst, comprising one or more transition metals from groups 8, 9 and 10 of the Periodic Table of the Elements, is important in catalyzing the formation of the genuinely active tungsten species needed for the cleavage of the carbon-carbon bonds and the formation of alkylene glycol precursors (such as glycolaldehyde and glyceraldehyde).

Inventors, however, have now found that, if operated for a prolonged period of time, an increasing amount of tungsten species appears to deposit onto the surface of the heterogeneous catalyst, increasingly preventing the heterogeneous catalyst from catalyzing the hydrogenation of the alkylene glycol precursors (such as glycolaldehyde and glyceraldehyde) to the alkylene glycol. As illustrated by the examples this imbalance causes a peak in selectivity to alkylene glycol followed by a sharp decline in alkylene glycol selectivity and further followed by humin formation.

The above finding led to a complex dilemma. On the one hand the tungsten deposits on the heterogeneous catalyst appear necessary to obtain the desired cleavage of the carbon-carbon bonds and without them mainly sorbitol is formed and the ethylene glycol selectivity suffers. On the other hand the tungsten deposits appear to lead, after a peak in ethylene glycol selectivity, to deactivation of the heterogeneous catalyst and humin formation.

The discovery of this previously unrecognized problem caused the inventors to recognize the need to maintain an appropriate balance. The inventors have now surprising found that with the claimed process, respectively the claimed catalyst system, the balance can be maintained and a process capable of being operated over a prolonged period of time can be obtained.

Contrary to expectations, inventors have found that the continuous or periodical provision of additional heterogeneous catalyst to the reactor results in a reduction of ethylene glycol selectivity, allowing one to use the ethylene glycol selectivity as an indicator for catalyst balance. By maintaining the ethylene glycol selectivity, for example below a certain threshold, by continuously or periodically providing additional heterogeneous catalyst to the reactor the process can be steered towards the desired long runtime.

BRIEF DESCRIPTION OF THE DRAWINGS

The invention is illustrated by the following figures:
FIG. 1 shows a graph of the glucose conversion results and ethylene glycol selectivity results of example 2.

DETAILED DESCRIPTION OF THE INVENTION

Preferably the reaction of carbohydrate source is preceded by a step wherein the carbohydrate source, the solvent, hydrogen and the homogeneous catalyst are provided to the reactor. In addition also a heterogeneous catalyst, suitably a first heterogeneous catalyst, which heterogeneous catalyst contains one or more transition metals from groups 8, 9 and 10 of the Periodic Table of the Elements, can be provided to such reactor.

By a carbohydrate source is herein understood a source of carbohydrates. The carbohydrate source can be selected from a variety of sources. Preferably, the carbohydrate source comprises one or more carbohydrates chosen from the group consisting of polysaccharides, oligosaccharides, disaccharides, monosaccharides and mixtures thereof.

Suitable examples may include, preferably sustainable, sources of carbohydrates such as cellulose, hemicellulose, starch, sugars, such as sucrose, mannose, arabinose, glucose, fructose and mixtures thereof. Carbohydrate sources that contain the above carbohydrates may include dextrose syrups, maltose syrups, sucrose syrups, glucose syrups, crystalline sucrose, crystalline glucose, wheat starch, corn starch, potato starch, cassava starch, and other carbohydrate containing streams, for example paper pulp streams, wood waste, paper waste, agricultural waste, cellulosic residues recovered from municipal waste, paper, cardboard, sugar cane, sugar beet, wheat, rye, barley, corn, rice, potatoes, cassava, other agricultural crops and combinations thereof. These streams may require pre-treatment to extract the carbohydrates (for example wet milling in the case or corn) or to remove components that interfere with the current process such as basic fillers (for example the removal of calcium carbonate in waste paper). In this way the process according to the invention can use natural sources, but can also be used to upgrade and usefully re-use waste streams. Preferably, the carbohydrates in the carbohydrate source are chosen from the group consisting of cellulose, hemicellulose, starch, glucose, sucrose, fructose, glucose-oligomers and combinations thereof. Since cellulose presents difficulties that are absent in other carbohydrate sources, the carbohydrate source is most preferably selected from the group consisting of starch, hemicelluloses and hemicellulosic sugars, glucose and mixtures thereof. Most preferably the carbohydrate source comprises or consists of glucose, fructose, sucrose or a combination thereof.

Suitably, the carbohydrate source can be provided to the reactor together with at least part of a solvent. More preferably, the carbohydrate source is partially or wholly dissolved in such a solvent. Preferences for such solvent are provided below. The solvent can for example be an aqueous medium, an organic medium including alkylene glycols, or a mixture containing water, diols and/or other polyols. Many carbohydrates are soluble in water or a mixture containing water, diols and/or other polyols. The carbohydrate source can also be provided to the reactor in the form of a slurry. Examples of such slurries include aqueous mixtures of water and hemicellulose, hemicellulosic sugars, glucose and/or starch.

The present process advantageously allows for the provision to the reactor of a very concentrated feed stream containing the carbohydrate source. When employing such a concentrated feed stream the process economics benefit. Such a feed stream may suitably comprise the carbohydrate source and a solvent, for example water and/or diols and/or other polyols. Preferably the carbohydrate source is provided to the reactor by a feed stream containing the carbohydrate source and a solvent, wherein such feed stream preferably contains in the range from equal to or more than 1.0 wt. % (weight percent), preferably equal to or more than 2.0 wt. %, more preferably equal to or more than 5.0 wt. %, still more preferably equal to or more than 10.0 wt. %, and most preferably equal to or more than 20.0 wt. % carbohydrate source, to equal to or less than 90.0 wt. %, preferably equal to or less than 70.0 wt. % and more preferably equal to or less than 50.0 wt. % carbohydrate source, based on the total weight of the carbohydrate source and solvent. A feed stream containing carbohydrate source within this concentration range can suitably be easily transported. The feed stream can also consist of only carbohydrate source.

For practical purposes the carbohydrate source can be provided to the reactor by a feed stream containing the carbohydrate source and a solvent, wherein such feed stream contains in the range from equal to or more than 2.0 wt. %, more preferably equal to or more than 10.0 wt. % to equal to or less than 30.0 wt. % of carbohydrate source, based on the total weight of the carbohydrate source and solvent. Such solvent may comprise any of the solvents mentioned below, but is preferably water. Most preferably the carbohydrate source is provided to the reactor by a feed stream containing the carbohydrate source and water, wherein such feed stream contains in the range from equal to or more than 2.0 wt. % to equal to or less than 30.0 wt. % of carbohydrate source, based on the total weight of the carbohydrate source and water.

Preferably the carbohydrate source is continuously or periodically added to the reactor. Preferably the carbohydrate source is provided to the reactor under a blanket of inert gas, such as nitrogen.

Solvent can be supplied as part of a feed stream comprising carbohydrate source, as described above. It is also possible for the solvent to be provided to the reactor separately or independently from the carbohydrate source.

Preferably a feed stream is used containing the carbohydrate source and solvent. The concentration of carbohydrate source in such a feed stream may suitably be adjusted such that sufficient solvent is provided to the reactor.

The solvent is preferably selected from the group consisting of water; organic solvents, such as diols and/or other polyols; and mixtures thereof. Suitably the solvent can be a mixture of water and one or more organic solvents. Alkanols are preferred as organic solvent. Such alkanols can be mono-alkanols, preferably water-miscible mono-alkanols, such as methanol, ethanol, propanol, butanol and mixtures thereof. For the process according to the invention, such light mono-alkanols are, however, less preferred. The alkanol can also be a water-miscible diol or other polyol, e.g. ethylene glycol, propylene glycol, butylene glycol, glycerol, xylytol, sorbitol or erythritol. By a dial is herein understood an organic compound comprising two hydroxyl groups. Preferably the solvent comprises an alkylene glycol. Examples of preferred alkylene glycols include ethylene glycol, propylene glycol, butylene glycol and mixtures thereof. The use of alkylene glycol is especially advantageous as it has been found that diols and/or polyols, including alkylene glycols, facilitate the dissolution of tungsten or a tungsten compound into the solvent, thereby promoting the catalytic activity of the tungsten or tungsten compound. It has further been found that the selectivity of the reaction to alkylene glycols is enhanced by the use of alkylene glycol as component in the solvent. Without wishing to be bound by any theory, it is believed that tungsten forms complexes with alkylene glycol whereby the conversion to by-products is reduced. Moreover, the use of an alkylene glycol as solvent does not involve the introduction of an extraneous reagent into the reaction mixture, which represents a further advantage. Preferably the solvent comprises or consists of water, one or more alkylene glycols, one or more alkanols, optionally one or more polyols, or a mixture of two or more thereof.

Preferably the solvent is continuously or periodically added to the reactor. At the same time a portion of the solvent may be continuously or periodically withdrawn from the reactor.

The hydrogen can be provided to the reactor as substantially pure hydrogen. Alternatively, the hydrogen may be supplied in the form of a mixture of hydrogen and an inert gas. The inert gas can suitably be selected from nitrogen, argon, helium, neon and mixtures thereof. More preferably, only hydrogen is used as gas in the process according to the invention.

Hydrogen can suitably be provided via a dip tube, for example a dip tube close to an agitator, or via a distributor, for example a sparger, to the reactor. Via such dip tube or distributor and optionally via one or more stirring mechanisms, hydrogen can be dissolved in the reaction mixture. Preferably the hydrogen is continuously or periodically added to the reactor.

The total pressure during the reaction comprises the vapour pressure of the solvent and the reactants at the temperature and pressure applied, in addition to the partial pressure of the hydrogen and, if present, the partial pressure of any inert gas.

The hydrogen partial pressure applied preferably lies in the range from equal to or more than 1.0 MegaPascal (MPa), preferably equal to or more than 2.0 MPa, more preferably equal to or more than 3.0 MPa to equal to or less than 16.0 MPa, preferably equal to or less than 12.0 MPa, more preferably equal to or less than 8.0 MPa. All pressures herein are absolute pressures.

The total pressure applied during the reaction is suitably at least 1.0 MPa, preferably at least 2.0 MPa abs, more preferably at least 3.0 MPa The total pressure applied during the reaction is suitably at most 16.0 MPa, more preferably at most 10.0 MPa Preferably the reactor is pressurized with hydrogen before addition of any starting material. The person skilled in the art will understand that the pressure at 20° C. will be lower than the actual pressure at the reaction temperature. The pressure applied during the reaction when converted back to 20° C., preferably equals a pressure in the range from equal to or more than 0.7 MPa to equal to or less than 8.0 MPa.

As explained before, the pressure may be applied by hydrogen gas or a hydrogen-containing gas, optionally in combination with the partial pressures of the contents of the reaction mixture. When the reaction mixture is heated the total pressure during the reaction is suitably in the range from 1.0 MPa wt. % to 16.0 MPa.

It is preferred to maintain the partial hydrogen pressure at the reaction temperature within such range from 1.0 MPa to 16.0 MPa, preferably during the entire reaction. Therefore hydrogen or a hydrogen-containing gas is preferably continuously introduced into the reaction mixture during reaction as explained above.

As indicated above, the pressure may be applied by hydrogen gas or a hydrogen-containing gas. When a hydrogen-containing gas is used, the hydrogen content in the hydrogen-containing gas is suitably up to 100 vol %. Most preferably a pure hydrogen gas is used to apply the pressure. During the reaction hydrogen is consumed, the hydrogen is therefore preferably supplied in a continuous or semi-continuous manner.

In the reactor at least a portion of the carbohydrate source is reacted in the presence of the hydrogen at a temperature in the range from equal to or more than 170° C. to equal to or less than 270° C. More preferably at least a portion of the carbohydrate source is reacted in the presence of the hydrogen at a temperature in the range from equal to or more than 200° C. to equal to or less than 250° C. The reactor may be brought to a temperature within these ranges before addition of any starting material and can be maintained at a temperature within the range.

The process includes reacting, in a reactor, at a temperature in the range from equal to or more than 170° C. to equal to or less than 270° C., at least a portion of a carbohydrate source in the presence of hydrogen, a solvent, and a catalyst system. The process is suitably yielding ethylene glycol.

The catalyst system includes:
a homogeneous catalyst, which homogeneous catalyst contains tungsten; and
a heterogeneous catalyst, which heterogeneous catalyst contains one or more transition metals from groups 8, 9 and 10 of the Periodic Table of the Elements supported on a carrier.

The homogeneous catalyst contains tungsten and is herein also referred to as tungsten-comprising homogenous catalyst.

The tungsten can be present as elemental tungsten or as a tungsten compound. The homogeneous catalyst can suitably contain one or more tungsten compounds. The tungsten or tungsten compound(s) can suitably be dissolved in the reaction mixture. Preferably, the tungsten has an oxidation state of at least +2. More preferably the tungsten has an oxidation state of +4, +5 or +6. When dissolved in the solvent, or respectively the reaction mixture, the dissolved tungsten or dissolved tungsten compound may form complexes with (other) components of the solvent, or respectively the reaction mixture.

The homogeneous catalyst provided to the reactor can be freshly made homogeneous catalyst or recycled homogeneous catalyst. Freshly made homogeneous catalyst is herein also referred to as "virgin" homogeneous catalyst. Such virgin homogeneous catalyst is preferably selected from the group consisting of tungstic acid ($H_2WO_4$) and tungstate compounds, such as tungstate salts, for example comprising at least one Group 1 or 2 element, for example sodium tungstate ($Na_2WO_4$) or potassium tungstate ($K_2WO_4$) or for example comprising ammonium tungstate. It is also possible to use a combination of one or more of these.

Suitably the homogeneous catalyst provided to the reactor can contain recycled homogeneous catalyst or a combination of virgin homogeneous catalyst and recycled homogeneous catalyst. The homogeneous catalyst provided to the reactor in the current invention can for example contain or consist of recycled tungsten species recovered, directly or indirectly (for example via distillation) from the effluent of a reactor.

Any recycled homogeneous catalyst may contain tungsten as a complex with components from the solvent in which such homogeneous catalyst may be dissolved. The recycled homogeneous catalyst may therefore suitably comprise tungsten in a form derived from a precursor tungsten compound, such as the above virgin homogeneous catalyst, as originally provided. The homogeneous catalyst provided to the reactor in the current invention can contain or consist of recycled tungsten species recovered, directly or indirectly (for example via a distillation), from the effluent of the reactor.

Preferably the homogeneous catalyst contains a tungsten compound or tungsten derived from a tungsten compound, wherein such tungsten compound is selected from the group consisting of tungstic add ($H_2WO_4$), tungsten bronze (present as $H_xWO_3$ or $M_xWO_3$, wherein x is a variable smaller than 1 (<1) and M is a metal, for example an alkali or alkali earth metal), ammonium tungstate, ammonium metatungstate, ammonium paratungstate, tungstate compounds comprising at least one Group 1 or 2 element, metatungstate compounds comprising at least one Group 1 or 2 element, paratungstate compounds comprising at least one Group 1 or 2 element, tungsten dioxide, tungsten trioxide ($WO_3$), heteropoly compounds of tungsten, and combinations thereof. Tungstic acid ($H_2WO_4$), tungsten bronze ($H_xWO_3$) and tungstate compounds comprising at least one Group 1 or 2 element, for example sodium tungstate ($Na_2WO_4$) or potassium tungstate ($K_2WO_4$), are preferred. Most preferably the homogeneous catalyst contains a tungsten compound or tungsten derived from a tungsten compound, wherein such tungsten compound is sodium tungstate and/or tungstic acid and/or tungsten bronze.

It has been found that the catalytic activity of the tungsten or tungsten compound advantageously increases if the tungsten or suitably the tungsten compound is dissolved. Preferably the homogeneous catalyst is continuously or periodically added to the reactor. Preferably such homogeneous catalyst that is continuously or periodically added contains tungsten that has an oxidation state of at least +2, more preferably at least +4. Preferably the homogeneous catalyst is chosen from the group consisting of tungstic acid ($H_2WO_4$), tungsten bronze ($H_xWO_3$), sodium tungstate, a dissolved tungstate ion, a dissolved metatungstate ion and a dissolved paratungstate ion.

As the tungsten can be present in so many forms, the tungsten and/or tungsten compounds are herein also referred to as tungsten species. By a tungsten species is herein understood any compound containing or consisting of tungsten element in any kind of form or oxidation state.

When (partly) oxidized, the tungsten species is herein also referred to as tungstate species. By a tungstate species is herein understood any compound comprising a tungsten-oxide bond. Examples of tungstate species include tungsten dioxide and tungsten trioxide and tungsten bronze.

Preferably the homogeneous catalyst is dissolved in a solvent. Such solvent can be any solvent as described above. The composition of the solvent may vary during the process.

Whilst the reaction is carried out in the reactor, the solvent may be formed by the reaction mixture itself.

The amount of tungsten that is provided to the reactor is preferably such that the concentration thereof in the reactor is maintained substantially constant. By substantially constant is herein understood that the difference between the highest and the lowest amounts of tungsten does not vary more than 10% from the average amount of tungsten in the reactor. Preferably the process according to the invention is a continuous or semi-continuous process. Preferably the tungsten compound is continuously or periodically added to the reactor. At the same time a portion of the tungsten compound may be continuously or periodically withdrawn from the reactor, suitably via the reactor product stream. Whereas it is feasible to add tungsten periodically, it is preferred to provide for a continuous addition of tungsten to the reactor. More preferably the tungsten compound is added to the reactor as a solution of tungsten compound in the solvent.

Preferably the concentration of tungsten compound in the reaction mixture during the reaction ranges from equal to or more than 0.01 wt. % (corresponding to 100 parts per million by weight (ppmw)) to equal to or less than 10.0 wt. % of tungsten (calculated as tungsten metal), based on the total weight of the reaction mixture. More preferably the concentration of tungsten compound in the reaction mixture during the reaction ranges from equal to or more than 0.01 wt. %, preferably equal to or more than 0.05 wt. %, to equal to or less than 5.0 wt. %, to equal to or less than 1.0 wt. %, or even equal to or less than 0.5 wt. %, of tungsten (calculated as tungsten metal), based on the total weight of the reaction mixture.

The heterogeneous catalyst contains one or more transition metals from groups 8, 9 and 10 of the Periodic Table of the Elements. The transition metal(s) can be selected from a wide range of transition metals. Preferably the one or more transition metal(s) is/are selected from the group consisting of Cu, Fe, Ni, Co, Pt, Pd, Ru, Rh, Ir, Os and combinations thereof. More preferably the one or more transition metal(s) is/are selected from the group consisting of Ni, Pd, Pt, Ru, Rh, Ir and combinations thereof. It has been found that these metals give good yields. The transition metal can suitably be present in its metallic form or as its hydride or oxide or as another compound. As explained below, it is also possible for the transition metal to be present in a partly tungstated form.

The heterogeneous catalyst preferably comprises one or more transition metals from groups 8, 9 and 10 of the Periodic Table of the Elements, supported on a carrier. The carrier may be selected from a wide range of known carrier materials. Suitable carriers include activated carbon, silica, zirconia, alumina, silica-alumina, titania, niobia, iron oxide, tin oxide, zinc oxide, silica-zirconia, zeolitic aluminosilicates, titanosilicates, magnesia, silicon carbide, clays and combinations thereof. By activated carbon is herein understood an amorphous form of carbon with a surface area of at least 800 $m^2/g$. Such activated carbon suitably has a porous structure. Most preferred carriers are activated carbon, silica, silica-alumina and alumina. More preferably, the heterogeneous catalysts comprise ruthenium and/or nickel as the transition metal and activated carbon as the carrier. Most preferably the heterogeneous catalyst contains ruthenium and/or nickel supported on activated carbon. Most preferably the heterogeneous catalyst contains ruthenium, preferably supported on activated carbon Preferably the heterogeneous catalyst comprises in the range from equal to or more than 1.0 wt. % to equal to or less than 50.0 wt. % of transition metal, more preferably equal to or more than 2.0 wt. % to equal to or less than 20.0 wt. % transition metal, on the basis of the total weight of transition metal and carrier.

It is possible for the heterogeneous catalyst to comprise more than one metal. Suitably, the heterogeneous catalyst can comprise at least one noble metal, selected from the group consisting of Pd, Pt, Ru, Rh and Ir, in combination with a second transition metal selected from the group of transition metals from groups 8, 9 or 10 of the Periodic Table of the Elements. The heterogeneous catalysts can for example comprise a combination of metals, for example Ni/Ir, Ni/Pt, Ni/Pd, Ni/Ru, Ru/Ir, Ru/Pt or Ru/Pd.

Preferably a slurry of additional heterogeneous catalyst, for example together with solvent, can be periodically or continuously provided to the reactor. Preferably such a slurry of heterogeneous catalyst comprises in the range from equal to or more than 1 wt. %, more preferably equal to or more than 2 wt. %, still more preferably equal to or more than 5 wt. % to equal to or less than 90 wt. %, more preferably equal to or less than 70 wt. %, most preferably equal to or less than 50 wt. % of heterogeneous catalyst, based on the total weight of such slurry. Preferably such a slurry is a slurry of heterogeneous catalyst in water and/or an alkylene glycol, for example ethylene glycol and/or propylene glycol and/or glycerol.

It is also possible for the additional heterogeneous catalyst to be provided as a solid and added by means of a screw feed or auger device.

The weight ratio of the total amount of tungsten compound (calculated on metal basis) present in the reactor to the transition metal (calculated on metal basis) present in the reactor at any one point in time may vary between wide ranges. The weight ratio of weight tungsten to the total weight of transition metal, all calculated on metal basis, preferably ranges from equal to or more than 1:3000 to equal to or less than 50:1 (tungsten metal:transition metal weight ratio (wt/wt)). More preferably the weight ratio of weight tungsten to the total weight of transition metal, all calculated on metal basis, as provided to the first reactor preferably ranges from equal to or more than 1:200 to equal to or less than 50:1 (tungsten metal:transition metal weight ratio (wt/wt)).

More preferably the molar ratio of moles tungsten to the total moles transition metal, all calculated on metal basis, present in the reactor, preferably ranges from equal to or more than 1:1 to equal to or less than 25:1, more preferably from equal to or more than 2:1 to equal to or less than 20:1 (tungsten metal:transition metal mole ratio (moles/moles)).

The concentration of tungsten compound, calculated as tungsten metal, based on the weight of carbohydrate source introduced into the first reactor, preferably ranges from equal to or more than 0.1 wt. %, more preferably from equal to or more than 1 wt. % to equal to or less than 35 wt. %, more preferably from equal to or more than 0.2 wt. %, even more preferably from equal to or more than 2 wt. % to equal to or less than 25 wt. %.

The concentration of transition metal introduced per hour into the first reactor, based on the weight of carbohydrate source introduced per hour into the first reactor, preferably ranges from equal to or more than 0.001 wt. %, more preferably from equal to or more than 0.01 wt. %, even more preferably from equal to or more than 0.1 wt. %, still more preferably from equal to or more than 0.2 wt. % to equal to or less than 2.0 wt. %, more preferably to equal to or less than 1.0 wt. %.

The reactor can be any type of reactor known to be suitable for the production of ethylene glycol from a carbohydrate source. Preferably the reactor is an agitated or mixed reactor. The reactor can for example be a slurry reactor, an ebulated bed reactor, a fluidized bed reactor, a bubble reactor, an external recycle loop reactor, a continuous stirred tank reactor (CSTR) or another type of mechanically agitated reactor. Most preferably the reactor is a continuously stirred tank reactor (CSTR). The use of a CSTR is very advantageous for the present process as the CSTR provides an excellent means for diluting the eventual concentration of the carbohydrate in the CSTR, whereas the feed stream may comprise a high concentration of carbohydrate. At the same time the alkylene glycols that are produced by the reaction of the carbohydrate provide a medium wherein tungsten compounds may be dissolved, thereby benefiting the catalytic activity of the tungsten catalyst component.

The residence time in the reactor may vary. Preferably the mean residence time of the carbohydrate source in the reactor is at least 1 min. (By mean residence time is herein understood the average time spent by a material flowing at a volumetric rate "u" through a volume "V", as further explained in the handbook "Modeling of Chemical Kinetics and Reactor Design" by A. Kayode Coker, published in 2001 by Butterworth Heinemann). Preferably the mean residence time of the carbohydrate source is in the range from equal to or more than 1 minutes to equal to or less than 6 hours, more preferably from equal to or more than 3 minutes to 2 hours, most preferable in the range from equal to or more than 5 minutes to equal to or less than 45 minutes. If the carbohydrate source reacts quickly, however, the mean residence time may also be shorter than 5 minutes and even shorter than 3 minutes.

If a feed stream to the first reactor is used containing in the range of equal to or more than 20.0 wt. % of carbohydrate source, based on the total weight of the carbohydrate source and solvent, the mean residence time of the carbohydrate source in the first reactor is preferably equal to or more than 5 minutes, more preferably equal to or more than 10 minutes, and preferably equal to or less than 2 hours, more preferably equal to or less than 45 minutes. It is believed that such a longer mean residence time can advantageously assist to convert a feedstream with a higher concentration of carbohydrate source.

Preferably the process is operated at a weight hourly space velocity (WHSV), expressed as the mass of carbohydrate source per mass of transition metal, expressed as metal, per hour, in the range of 0.01 to 100 $hr^{-1}$, preferably from 0.05 to 10 $hr^{-1}$. For practical purposes a WHSVB in the range between 0.5 to 2.0 $hr^{-1}$ can be used.

As explained above, without wishing to be bound by any kind of theory, the present inventors believe that, if the process is operated for a prolonged period of time, an increased amount of tungsten species becomes deposited onto the surface of the heterogeneous catalyst, and especially the transition metal thereof. Such tungsten species may become adsorbed, may become complexed or may in another manner become deposited onto the surface of the transition metal. Such a transition metal that is (partly) covered with deposited tungsten species or tungstate species is herein also referred to as (partly) tungstated transition metal. Such a heterogeneous catalyst that is (partly) covered with deposited tungsten species or tungstate species is herein also referred to as (partly) tungstated heterogeneous catalyst. As a result of the deposited tungsten species or tungstate species the heterogeneous catalyst is believed to be increasingly prevented from catalyzing the hydrogenation of the mentioned alkylene glycol precursors, such as glycolaldehyde, to alkylene glycol, such as ethylene glycol. This in turn results in a decrease in selectivity towards ethylene glycol.

In the process according to the invention additional heterogeneous catalyst is continuously or periodically provided to the reactor. This additional heterogeneous catalyst allows one to restore the balance and suitably provides non-tungstated transition metal for the hydrogenation of the mentioned alkylene glycol precursors.

The partly or wholly tungstated heterogeneous catalyst, present in the reactor, and the less-tungstated or non-tungstated heterogeneous catalyst, that can be freshly provided to the reactor, may suitably differ in their molar ratio of moles tungsten to the total moles transition metal. The heterogeneous catalyst present in the reactor, that may suitably be (partly) tungstated, is therefore also referred to as a first heterogeneous catalyst, whilst the additional heterogeneous catalyst is also referred to as second heterogeneous catalyst.

The preferences for both such first heterogeneous catalyst as well as for such second heterogeneous catalyst are suitably as described above for the heterogeneous catalyst. Although the transition metal(s) may differ, the one or more transition metal(s) in the second heterogeneous catalyst are preferably the same as the one or more transition metal(s) in the first heterogeneous catalyst.

As indicated above, the first heterogeneous catalyst contains tungsten in addition to the one or more transition metals from groups 8, 9 and 10 of the Periodic Table of the Elements. The second heterogeneous catalyst either contains no tungsten; or contains an amount of tungsten in a molar ratio of moles tungsten to moles transition metal, all calculated on metal basis, that is less than the molar ratio of moles tungsten to moles transition metal of the first heterogeneous catalyst. If tungsten is present within the second heterogeneous catalyst, the molar ratio of moles tungsten to moles transition metal in the second heterogeneous catalyst is preferably at most ¾, more preferably at most ½, and most preferably at most ¼ of the molar ratio of moles tungsten to moles transition metal in the second heterogeneous catalyst.

Herein the first heterogeneous catalyst can therefore also sometimes be referred to as "tungsten-rich" catalyst, whilst the second heterogeneous catalyst can also sometimes be referred to as "tungsten-lean" catalyst.

Hence, most preferably the carbohydrate is reacted in the presence of a catalyst system including:
a) a homogeneous catalyst, that is residing in the reactor, which homogeneous catalyst contains tungsten;
b) a first heterogeneous catalyst, that is residing in the reactor, which first heterogeneous catalyst contains one or more transition metals from groups 8, 9 and 10 of the Periodic Table of the Elements supported on a carrier, and which first heterogeneous catalyst further contains an amount of tungsten; and
c) a second heterogeneous catalyst, that is continuously or periodically provided to the reactor, which second heterogeneous catalyst contains one or more transition metals from groups 8, 9 and 10 of the Periodic Table of the Elements supported on a carrier, and which second heterogeneous catalyst contains no tungsten; or an amount of tungsten in a molar ratio of moles tungsten to moles transition metal that is less than the molar ratio of moles tungsten to moles transition metal of the first heterogeneous catalyst; and wherein continuously or periodically the second heterogeneous catalyst is added to the reactor. Preferably the selectivity towards ethylene glycol is maintained by continuously or periodically adding the second heterogeneous catalyst to the reactor.
wherein the selectivity towards ethylene glycol is maintained by continuously or periodically adding the second heterogeneous catalyst to the reactor.

Such a balanced three-component catalyst system is believed to be novel and inventive in itself. The invention therefore further provides a catalyst system including:
a) a homogeneous catalyst, that may suitably be residing in a reactor, which homogeneous catalyst contains tungsten;
b) a first heterogeneous catalyst, that may suitably also be residing in the reactor, which first heterogeneous catalyst contains one or more transition metals from groups 8, 9 and 10 of the Periodic Table of the Elements supported on a carrier, and which first heterogeneous catalyst further contains an amount of tungsten;
c) a second heterogeneous catalyst, that may suitably be continuously or periodically added to the reactor, which second heterogeneous catalyst contains one or more transition metals from groups 8, 9 and 10 of the Periodic Table of the Elements supported on a carrier, and which second heterogeneous catalyst contains no tungsten; or an amount of tungsten in a molar ratio of moles tungsten to moles transition metal that is less than the molar ratio of moles tungsten to moles transition metal of the first heterogeneous catalyst.

The second heterogeneous catalyst may preferably contain no tungsten or an amount of tungsten in a molar ratio of moles tungsten to moles transition metal of less than 10:1, preferably less than 5:1 and more preferably less than 2:1. Most preferably the second heterogeneous catalyst contains no tungsten or an amount of tungsten in a molar ratio of moles tungsten to moles transition metal of less than 1:1, still more preferably of less than 0.5:1.

Correspondingly, the first heterogeneous catalyst may preferably contain an amount of tungsten in a molar ratio of moles tungsten to moles transition metal of equal to or more than 10:1, equal to or more than 5:1 or equal to or more than 2:1. Most preferably the first heterogeneous catalyst contains an amount of tungsten in a molar ratio of moles tungsten to moles transition metal of equal to or more than 1:1.

More preferably the catalyst system includes:
a) a homogeneous catalyst, that may suitably be residing in a reactor, which homogeneous catalyst contains tungsten;
b) a first heterogeneous catalyst, that may suitably also be residing in the reactor, which first heterogeneous catalyst contains one or more transition metals from groups 8, 9 and 10 of the Periodic Table of the Elements supported on a carrier, and which first heterogeneous catalyst further contains an amount of tungsten in a molar ratio of moles tungsten to moles transition metal of equal to or more than 1:1;
c) a second heterogeneous catalyst, that may suitably be continuously or periodically provided to the reactor, which second heterogeneous catalyst contains one or more transition metals from groups 8, 9 and 10 of the Periodic Table of the Elements supported on a carrier, and which second heterogeneous catalyst contains no tungsten; or an amount of tungsten in a molar ratio of moles tungsten to moles transition metal of less than 1:1.

Preferably the second heterogeneous catalyst contains one or more transition metals from groups 8, 9 and 10 of the Periodic Table of the Elements supported on a carrier, wherein equal to or less than 80%, more preferably equal to or less than 60%, even more preferably equal to or less than 40%, still more preferably equal to or less than 20%, still even more preferably equal to or less than 10%, and most preferably equal to or less than 5%, of the total surface of the second heterogeneous catalyst (i.e. of the transition metal and the carrier) is covered with tungsten species, or more preferably tungstate species.

More preferably the second heterogeneous catalyst contains one or more transition metals from groups 8, 9 and 10 of the Periodic Table of the Elements supported on a carrier, wherein equal to or less than 80%, more preferably equal to or less than 60%, even more preferably equal to or less than 40%, still more preferably equal to or less than 20%, still even more preferably equal to or less than 10%, and most preferably equal to or less than 5%, of the available surface of the transition metal is covered with tungsten species, or more preferably tungstate species.

Preferably at least part, and preferably essentially all, of the tungsten in the first and/or second heterogeneous catalyst is present in the form of one or more deposited (for example, adsorbed, complexed or otherwise deposited) tungsten species. More preferably at least part, and preferably essentially all, of the tungsten in the first and/or second heterogeneous catalyst is present in the form of one or more deposited (for example, adsorbed, complexed or otherwise deposited) tungstate species.

Most suitably the first heterogeneous catalyst and/or the second heterogeneous catalyst comprise one or more tungstate compounds, preferably tungsten dioxide and/or tungsten trioxide, deposited onto the transitional metal and/or the carrier.

Preferences for such catalyst system are as described above. Conveniently the first heterogeneous catalyst and/or the second heterogeneous catalyst comprise one or more tungstate compounds, preferably tungsten dioxide and/or tungsten trioxide, deposited onto the transitional metal and/or the carrier. Further, the first heterogeneous catalyst and/or the second heterogeneous catalyst may suitably comprise a tungstate compound, wherein tungsten has an oxidation state of +4; and/or a tungstate compound, wherein tungsten has an oxidation state of +5; and/or a tungstate compound, wherein tungsten has an oxidation state of +6.

Conveniently, after addition, the second heterogeneous catalyst can be gradually tungstated or further tungstated inside the reactor to yield further first heterogeneous catalyst. That is, in the reactor tungsten species, suitably tungstate species, can conveniently deposit onto the added second heterogeneous catalyst and the second heterogeneous catalyst is converted into first heterogeneous catalyst. The conversion of second heterogeneous catalyst to first heterogenous catalyst can suitably be carried out in-situ, i.e. during the reaction.

The novel and inventive catalyst system therefore preferably comprises a first heterogeneous catalyst, with preferences as listed above, residing in a reactor and an additional second heterogeneous catalyst, with preferences as listed above, being continuously or periodically provided, that is, being continuously or periodically added, to such reactor.

The additional or second heterogeneous catalyst can be added to the reactor in any manner that is known to be suitable for such a purpose. Preferably the additional or second heterogeneous catalyst is provided, i.e. added, to the reactor as a slurry in a solvent. Preferences for such a solvent are as described above. Most preferably such a solvent comprises glycerol or an alkylene glycol, or a mixture of water and glycerol or a mixture of water and an alkylene glycol. It is also possible for the additional or second heterogeneous catalyst to be added to the reactor as a solid for example by means of a screw feed or auger device.

In the process according to the invention preferably continuously or periodically a portion of the first heterogeneous catalyst is withdrawn from the reactor. Such withdrawn first heterogeneous catalyst can suitably be replaced by the added second heterogeneous catalyst.

Thus advantageously a continuous or semi-continuous process is provided for the preparation of ethylene glycol from a carbohydrate source including:
(i) continuously reacting, in a reactor, at a temperature in the range from equal to or more than 170° C. to equal to or less than 270° C., at least a portion of a carbohydrate source in the presence of hydrogen, a solvent, and a catalyst system, to yield ethylene glycol;
wherein the catalyst system includes:
a homogeneous catalyst, which homogeneous catalyst contains tungsten;
a first heterogeneous catalyst, which first heterogeneous catalyst contains one or more transition metals from groups 8, 9 and 10 of the Periodic Table of the Elements supported on a carrier, and which first heterogeneous catalyst further contains an amount of tungsten;
(ii) continuously or periodically withdrawing a portion of the first heterogeneous catalyst from the reactor; and continuously or periodically adding a second heterogeneous catalyst to the reactor, which second heterogeneous catalyst contains one or more transition metals from groups 8, 9 and 10 of the Periodic Table of the Elements supported on a carrier, and which second heterogeneous catalyst contains no tungsten; or an amount of tungsten in a molar ratio of moles tungsten to moles transition metal that is less than the molar ratio of moles tungsten to moles transition metal of the first heterogeneous catalyst; and
(iii) continuously converting second heterogeneous catalyst to yield first heterogeneous catalyst.

Preferences for step (i), the first and the second heterogeneous catalyst are as described herein above and herein below.

Step (ii) is preferably carried as described herein above. Preferably in the range from equal to or more than 0.01 wt. %, more preferably equal to or more than 0.1 wt. %, still more preferably equal to or more than 0.5 wt. % to equal to or less than 10.0 wt. %, more preferably equal to or less than 5.0 wt. % of the first heterogeneous catalyst present in the reactor is periodically or continuously withdrawn and replaced by second heterogeneous catalyst.

Step (iii) preferably comprises the continuously tungstenating of the second heterogeneous catalyst. That is, step (iii) preferably comprises the continuous deposition of tungsten species, preferably tungstate species, onto the second heterogeneous catalyst. As a consequence, the molar ratio of moles tungsten to moles transition metal of the second heterogeneous catalyst increases such that first heterogeneous catalyst is obtained.

Preferably step (iii) is carried out inside the reactor. That is, preferably the second heterogeneous catalyst is gradually tungstated or further tungstated inside the reactor to yield further first heterogeneous catalyst.

Without wishing to be bound by any kind of theory, it is believed that the first heterogeneous catalyst and the second heterogeneous catalyst both have a function. Without the first heterogeneous catalyst, it is found that mainly sorbitol is formed and the ethylene glycol selectivity suffers. Without the second heterogeneous catalyst, it is found that humins are obtained.

The inventors have now surprising found that with the claimed process, respectively the claimed catalyst system, the balance can be maintained. Conveniently ethylene glycol selectivity can be used as an indicator for catalyst balance.

Preferably the ethylene glycol selectivity is maintained below a threshold by continuously or periodically adding additional heterogeneous catalyst to the reactor. By maintaining the ethylene glycol selectivity below a certain threshold by continuously or periodically adding additional heterogeneous catalyst to the reactor the process can advantageously be steered towards the desired long runtime.

Preferably the ethylene glycol selectivity is continuously or periodically determined. More preferably the ethylene glycol selectivity is monitored with in-line equipment.

The determined ethylene glycol selectivity can conveniently be compared with a pre-set threshold, for example set via a computer. Most preferably the ethylene glycol selectivity is continuously or periodically determined and compared with a one or more pre-set thresholds and additional heterogeneous catalyst is provided to the reactor if such a threshold is reached or exceeded.

Whenever the ethylene glycol selectivity threatens to exceed the threshold, an amount of additional, or second, heterogeneous catalyst can be provided to the reactor to reduce the ethylene glycol selectivity.

Preferably the threshold is an upper threshold. More preferably the threshold is 85%, even more preferably the threshold is 80%, still more preferably the threshold is 75%, still even more preferably the threshold is 70%, yet even more preferably the threshold is 65% and most preferably the threshold is 60%.

More preferably the ethylene glycol selectivity is maintained within a certain range. For example, the ethylene glycol selectivity can advantageously be maintained within a range of equal to or more than 35%, more preferably equal to or more than 40%, and most preferably equal to or more than 45% to equal to or less than 85%, more preferably to equal to or less than 80%, even more preferably to equal to or less than 75% and most preferably to equal to or less than 70%.

When the carbohydrate source is continuously or periodically added to the reactor, preferably the weight ratio of continuously or periodically provided additional or second heterogeneous catalyst to continuously or periodically added carbohydrate source is constantly kept within a range from 0.5:100 to 1.0:100.

After the reacting at least a portion of the carbohydrate source, a reactor product stream can be withdrawn from the reactor. This reactor product stream suitably contains the ethylene glycol (ethane-1,2-diol) yielded by the reaction. In addition, the reactor product stream can contain other compounds, such as unreacted carbohydrate source and one or more by-products such as diethylene glycol (2,2'-oxydi (ethan-1-ol)) propylene glycol (propane-1,2-diol), glycerol (propane-1,2,3-triol), butane-1,2-diol, butane-1,3-diol, butane-2,3-diol, butane-1,4-diol, methanol, ethanol, propanol, butanol, sorbitol (hexane-1,2,3,4,5,6-hexol) and/or erythritol (butane-1,2,3,4-tetraol).

The invention is further illustrated by the following non-limiting examples.

Comparative Example A

A 300 milliliter continuously stirred tank reactor (CSTR) of Hastelloy C276 was provided with a gas dispersion impeller operating at approximately 750 rpm.

The CSTR was filled with an amount of a heterogeneous 5 wt. % ruthenium on carbon catalyst (i.e. a 5 wt. % Ru/C catalyst) in an ultrapure water/glycerol solution, as listed in Table 1. No additional heterogeneous catalyst was provided during the reaction.

Subsequently a continuous carbohydrate feed containing about 10.8 wt. % glucose in ultrapure water and a continuous homogeneous catalyst feed containing 0.44 wt. % tungsten acid ($H_2WO_3$) in a mixture of ultrapure water and glycerol (about 50 wt. % water and about 50 wt. % glycerol, based on the total weight of water and glycerol), were separately pumped continuously into the CSTR. In addition sodium hydroxide was added in a molar ratio of tungstic acid to sodium hydroxide of 8.3. Hydrogen was fed to the reactor through a dip leg with a filter at the tip at a continuous rate of 8 grams/hour. The reaction temperature was kept at an average of about 220° C., the reaction pressure was kept at an average of about 65 bar gauge, corresponding to about 6.6 MegaPascal absolute. The system was operated with an average residence time of about 24 minutes.

A summary of the reaction conditions is provided in Table 1.

TABLE 1

Reaction conditions of Comparative example A

| | | | |
|---|---|---|---|
| Glucose Feed Conc., wt. % | 10.8 | Ru/C at SOR*, g | 9.19 |
| Tungsten Acid Conc., wt. % | 0.44 | Ultrapure Water, g | 200.0 |
| Residence Time, min | 24.0 | Glycerol, wt. % | 19.0 |
| Ru/C Added, g | — | $H_2WO_4$:NaOH (moles:moles) | 8.3 |
| Temperature, ° C. | 220 | Reaction pressure (barg) | 65 |

*SOR: Start of Reaction

After the start of the reaction, the ethylene glycol (EG) selectivity continued to increase until an EG selectivity of about 76% was reached at hour 18. Then EG selectivity began to decline rapidly between hours 18 and 22. At 22 hours the EG selectivity was about 59%. Humins formation was also noticeable in samples collected during the fast decline.

Comparative example A was terminated after 31 hours of operation due to low EG selectivity and humins formation. At 31 hours the EG selectivity was about 15%.

Example 1

Example 1 was carried out in the same CSTR and under similar conditions as Comparative Example A.

A slurry of heterogeneous catalyst was prepared by mixing 90 grams of glycerol, 90 grams of ultrapure water and 10 grams of a heterogeneous 5 wt. % ruthenium on carbon catalyst (i.e. a 5 wt. % Ru/C catalyst).

At the start of the reaction the CSTR was filled with part of this mixture, such that 9.19 grams of Ru/C were loaded into the CSTR. In addition a number of cartridges were prepared, each cartridge containing a mixture of 4.5 grams of glycerol and 4.5 grams of ultrapure water along with 0.5 grams of the 5 wt. % Ru/C catalyst.

Subsequently a continuous carbohydrate feed containing about 10.8 wt. % glucose in ultrapure water and a continuous homogeneous catalyst feed containing 0.43 wt. % tungsten acid ($H_2WO_3$) in a mixture of ultrapure water and glycerol (about 50 wt. % water and about 50 wt. % glycerol, based on the total weight of water and glycerol), were separately pumped continuously into the CSTR. In addition sodium hydroxide was added in a molar ratio of tungstic acid to sodium hydroxide of 6.4. Hydrogen was fed to the reactor through a dip leg with a filter at the tip at a continuous rate of 8 grams/hour.

The reaction temperature was kept at an average of about 220° C., the reaction pressure was kept at an average of about 63 bar gauge, corresponding to about 6.4 MegaPascal absolute. The system was operated with an average residence time of about 24 minutes. A summary of the reaction conditions is provided in Table 2.

TABLE 2

Reaction conditions of Example 1

| | | | |
|---|---|---|---|
| Glucose Feed Conc., wt. % | 10.8 | Ru/C at SOR*, g | 9.19 |
| Tungsten Acid Conc., wt. % | 0.43 | Ultrapure Water, g | 200.1 |
| Residence Time, min | 24.0 | Glycerol, wt. % | 18.9 |
| Ru/C Added, g | 5.9 | $H_2WO_4$:NaOH (moles:moles) | 6.4 |
| Temperature, ° C. | 220 | Reaction pressure (barg) | 63 |

*SOR: Start of Reaction

After the start of the reaction, the initial ethylene glycol (EG) selectivity gradually increased. After 24 hours of operation, when EG selectivity reached about 58%, one of the above mentioned cartridges was used to inject approximately 0.5 g of fresh Ru/C catalyst dissolved in a solution of 4.5 grams of glycerol and 4.5 grams of ultrapure water, into the reactor. An immediate increase in sorbitol selectivity, and a decrease in EG selectivity was observed. Several hours later, the EG selectivity and sorbitol selectivity began to recover and fall, respectively. Once the EG selectivity reached about 58% again (at about 31 hours), another cartridge was used to inject approximately 0.5 g of fresh Ru/C catalyst into the reactor. This procedure was repeated for the rest of the run, with the interval between injections varying from 3 to 10 hours. In all, approximately 5.5 grams of (wet) additional Ru/C catalyst were added during the reaction in Example 1. As the slurry catalyst mixture was prepared at ambient temperature, containing 50/50 (w/w) glycerol and water, each Ru/C slurry injection resulted in a momentarily drop in reactor temperature and caused a temporary disturbance in the effluent composition.

The system was operated for a total of 90 hours of runtime. At hour 90, the EG selectivity was about 63% and sorbitol selectivity was about 6%. In the period after the initial period of 24 hours, an average selectivity towards ethylene glycol of about 49% was achieved.

Spent Ru/C catalyst was isolated from the system, dried and stored and subsequently analyzed. In addition to ruthenium and carbon, the spent catalyst was found to also contain deposited tungsten species. Analysis by Inductively coupled Plasma (ICP) indicated that the spent catalyst contained about 4.2 wt. % ruthenium and about 5.6 wt. % tungsten, corresponding to a molar ratio of moles tungsten to moles ruthenium of about 0.73. It is, however, unknown if any tungsten species may have washed away in the work-up process. X-ray absorption spectroscopy (XANES/XES) of the dried spent catalyst indicated the presence of 79 wt. % $WO_3$ and 21 wt. % $WO_2$ components.

Example 2

Example 2 was carried out as example 1, except that a slightly lower concentration of glucose was used for the feed (i.e. 9.1 wt. %) and a slightly lower concentration of tungsten acid (i.e. 0.40 wt. %) was used.

Again, a slurry of heterogeneous catalyst was prepared by mixing 90 grams of glycerol, 90 grams of ultrapure water and 10 grams of a heterogeneous 5 wt. % ruthenium on carbon catalyst (i.e. a 5 wt. % Ru/C catalyst).

At the start of the reaction the CSTR was filled with part of this mixture, such that 9.19 grams of Ru/C were loaded into the CSTR. In addition a number of cartridges were prepared, each cartridge containing a mixture of 4.5 grams of glycerol and 4.5 grams of ultrapure water along with 0.5 grams of the 5 wt. % Ru/C catalyst.

A summary of the reaction conditions for example 2 is provided in Table 3.

TABLE 3

Reaction conditions of Example 2

| | | | |
|---|---|---|---|
| Glucose Feed Conc., wt. % | 9.1 | Ru/C at SOR*, g | 9.19 |
| Tungsten Acid Conc., wt. % | 0.40 | Ultrapure Water, g | 200.0 |
| Residence Time, min | 24.0 | Glycerol, wt. % | 19.0 |
| Ru/C Added, g | 15.2 | $H_2WO_4$:NaOH (moles:moles) | 7.2 |
| Temperature, ° C. | 220 | Reaction pressure (barg) | 63 |

*SOR: Start of Reaction

The glucose conversion results, ethylene glycol (EG) selectivity results and sorbitol selectivity results of Example 2 are illustrated in Table 4 and FIG. 1. At the hours where catalyst was injected, the samples were taken prior to such catalyst injections.

After the start of the reaction the initial EG selectivity showed a faster climb than in Example 1, with EG selectivity reaching a selectivity of about 57% in 14 hours. This was partially due to the slightly lower glucose feed concentration.

Catalyst injections took place on average between 2 and 5 hours, as ethylene glycol selectivity swung less and recovered faster than in Example 1. In order to prevent EG selectivity from exceeding 55%, in some instances catalyst was injected rather frequently as the EG selectivity trended higher than in Example 1. In all, about 14 of Ru/C catalyst were added to the reactor in Example 2.

The system was operated for a total of 102 hours of runtime. At hour 102, the EG selectivity was about 56% and sorbitol selectivity was about 10%. In the period after the initial period of 14 hours, an average selectivity towards ethylene glycol of about 61% was achieved.

Analysis by Inductively coupled Plasma (ICP) indicated that the spent catalyst contained 1.5 wt. % ruthenium and 48 wt. % tungsten. The tungsten ruthenium molar ratio can be calculated to be about 17.6

TABLE 4

Results of Example 2

| | Runtime (hr) | | | | | | | | | |
|---|---|---|---|---|---|---|---|---|---|---|
| | 1 | 2 | 3 | 4 | 5 | 6 | 7 | 8 | 9 | 10 |
| Ru/C (gr) | | | | | | | | | | |
| Conv. (%) | 100.0 | 99.8 | 99.7 | 99.7 | 99.7 | 99.7 | 99.7 | 99.7 | 99.7 | 99.7 |
| EG Sel (%) | 13.3 | 12.7 | 24.8 | 34.7 | 40.7 | 44.7 | 48.0 | 46.7 | 48.1 | 52.0 |
| SB Sel (%) | 0.6 | 41.6 | 36.1 | 28.2 | 23.7 | 21.0 | 19.4 | 20.0 | 18.6 | 15.7 |

| | Runtime (hr) | | | | | | | | | |
|---|---|---|---|---|---|---|---|---|---|---|
| | 11 | 12 | 13 | 14 | 15 | 16 | 17 | 18 | 19 | 20 |
| Ru/C (gr) | | | | 0.5 | | | 0.5 | | | |
| Conv. (%) | 99.8 | 99.8 | 99.8 | 99.8 | 99.8 | 99.7 | 99.8 | 99.8 | 99.8 | 99.8 |
| EG Sel (%) | 54.1 | 55.0 | 56.1 | 57.2 | 52.3 | 51.1 | 55.4 | 52.7 | 53.1 | 56.2 |
| SB Sel (%) | 14.7 | 14.6 | 13.5 | 12.9 | 16.1 | 16.3 | 13.4 | 14.9 | 14.6 | 12.2 |

| | Runtime (hr) | | | | | | | | | |
|---|---|---|---|---|---|---|---|---|---|---|
| | 21 | 22 | 23 | 24 | 25 | 26 | 27 | 28 | 29 | 30 |
| Ru/C (gr) | 0.5 | | | | 0.5 | | | | 0.5 | |
| Conv. (%) | 99.8 | 99.8 | 99.8 | 99.8 | 99.9 | 99.9 | 99.8 | 99.9 | 99.9 | 99.8 |
| EG Sel (%) | 60.0 | 57.0 | 57.8 | 61.0 | 62.9 | 61.0 | 61.0 | 64.0 | 66.0 | 61.9 |
| SB Sel (%) | 10.7 | 11.6 | 11.3 | 10.1 | 8.8 | 9.3 | 9.4 | 8.2 | 7.2 | 10.2 |

| | Runtime (hr) | | | | | | | | | |
|---|---|---|---|---|---|---|---|---|---|---|
| | 31 | 32 | 33 | 34 | 35 | 36 | 37 | 38 | 39 | 40 |
| Ru/C (gr) | 0.5 | | | 0.5 | | | 0.5 | | 0.5 | |
| Conv. (%) | 99.8 | 99.8 | 99.8 | 99.9 | 99.8 | 99.9 | 99.9 | 99.9 | 99.9 | 99.9 |
| EG Sel (%) | 58.2 | 57.5 | 61.5 | 67.7 | 63.9 | 65.3 | 69.1 | 63.6 | 67.6 | 65.4 |
| SB Sel (%) | 10.1 | 10.1 | 7.6 | 5.9 | 7.9 | 7.2 | 5.6 | 5.9 | 5.4 | 5.9 |

| | Runtime (hr) | | | | | | | | | |
|---|---|---|---|---|---|---|---|---|---|---|
| | 41 | 42 | 43 | 44 | 45 | 46 | 47 | 48 | 49 | 50 |
| Ru/C (gr) | 0.5 | | 0.5 | | 0.5 | | 0.5 | | | |
| Conv. (%) | 99.9 | 99.9 | 99.9 | 99.9 | 99.9 | 99.9 | 99.9 | 99.9 | 99.9 | 99.9 |

TABLE 4-continued

Results of Example 2

| | | | | | | | | | | |
|---|---|---|---|---|---|---|---|---|---|---|
| EG Sel (%) | 65.9 | 65.8 | 65.1 | 62.4 | 62.5 | 59.9 | 61.8 | 66.1 | 69.4 | 64.3 |
| SB Sel (%) | 4.9 | 5.7 | 6.9 | 7.1 | 7.2 | 8.0 | 7.5 | 6.2 | 4.9 | 6.2 |

| | Runtime (hr) | | | | | | | | | |
|---|---|---|---|---|---|---|---|---|---|---|
| | 51 | 52 | 53 | 54 | 55 | 56 | 57 | 58 | 59 | 60 |
| Ru/C (gr) | 0.5 | | 0.5 | | 0.5 | | 0.5 | | | 0.5 |
| Conv. (%) | 99.9 | 99.9 | 99.9 | 99.9 | 99.9 | 99.9 | 99.9 | 99.9 | 99.9 | 99.9 |
| EG Sel (%) | 65.1 | 61.7 | 61.9 | 59.6 | 62.8 | 59.9 | 57.5 | 57.4 | 61.3 | 63.5 |
| SB Sel (%) | 6.0 | 7.5 | 7.2 | 7.6 | 7.1 | 9.0 | 9.8 | 8.4 | 7.2 | 6.4 |

| | Runtime (hr) | | | | | | | | | |
|---|---|---|---|---|---|---|---|---|---|---|
| | 61 | 62 | 63 | 64 | 65 | 66 | 67 | 68 | 69 | 70 |
| Ru/C (gr) | | 0.5 | | | 0.5 | | | | 0.5 | |
| Conv. (%) | 99.9 | 99.9 | 99.9 | 99.9 | 99.9 | 99.8 | 99.9 | 99.9 | 99.9 | 99.9 |
| EG Sel (%) | 62.8 | 65.1 | 66.8 | 66.5 | 63.6 | 57.2 | 56.6 | 61.3 | 63.9 | 62.7 |
| SB Sel (%) | 6.3 | 6.1 | 5.2 | 8.0 | 7.3 | 10.6 | 10.2 | 7.8 | 5.8 | 6.6 |

| | Runtime (hr) | | | | | | | | | |
|---|---|---|---|---|---|---|---|---|---|---|
| | 71 | 72 | 73 | 74 | 75 | 76 | 77 | 78 | 79 | 80 |
| Ru/C (gr) | 0.5 | | | | 0.5 | | | | 0.5 | |
| Conv. (%) | 99.9 | 99.9 | 99.9 | 99.9 | 99.7 | 99.9 | 99.9 | 99.9 | 99.9 | 99.9 |
| EG Sel (%) | 62.6 | 59.0 | 59.7 | 62.2 | 63.9 | 60.4 | 60.8 | 61.9 | 63.5 | 62.3 |
| SB Sel (%) | 6.6 | 7.5 | 7.8 | 6.8 | 6.2 | 7.2 | 6.8 | 6.4 | 5.7 | 7.3 |

| | Runtime (hr) | | | | | | | | | |
|---|---|---|---|---|---|---|---|---|---|---|
| | 81 | 82 | 83 | 84 | 85 | 86 | 87 | 88 | 89 | 90 |
| Ru/C (gr) | | | 0.5 | | | | 0.5 | | | |
| Conv. (%) | 99.9 | 99.9 | 99.9 | 99.9 | 99.9 | 99.9 | 99.9 | 99.8 | 99.9 | 99.8 |
| EG Sel (%) | 60.5 | 62.2 | 64.9 | 62.2 | 62.7 | 63.8 | 67.0 | 58.9 | 54.1 | 49.9 |
| SB Sel (%) | 8.6 | 6.8 | 5.1 | 5.9 | 5.9 | 5.8 | 5.0 | 12.4 | 9.0 | 14.9 |

| | Runtime (hr) | | | | | | | | | |
|---|---|---|---|---|---|---|---|---|---|---|
| | 91 | 92 | 93 | 94 | 95 | 96 | 97 | 98 | 99 | 100 |
| Ru/C (gr) | | | | | 0.5 | | | | | |
| Conv. (%) | 99.9 | 99.9 | 99.9 | 99.9 | 100.0 | 99.9 | 99.9 | 99.9 | 99.9 | 99.9 |
| EG Sel (%) | 52.4 | 56.9 | 60.5 | 64.5 | 65.7 | 63.7 | 58.6 | 60.8 | 63.6 | 65.0 |
| SB Sel (%) | 13.4 | 8.9 | 6.7 | 5.3 | 4.2 | 5.9 | 7.4 | 6.8 | 6.1 | 5.6 |

| | Runtime (hr) | |
|---|---|---|
| | 101 | 102 |
| Ru/C (gr) | | |
| Conv. (%) | 99.9 | 99.9 |
| EG Sel (%) | 60.8 | 55.6 |
| SB Sel (%) | 8.2 | 10.0 |

Ru/C = amount of additional heterogeneous 5 wt % ruthenium on carbon catalyst (grams)
Conv = glucose conversion (%)
EG Sel. = Ethylene glycol selectivity (%)
SB Sel. = Sorbitol selectivity (%)

The invention claimed is:

1. A continuous or semi-continuous process for the preparation of ethylene glycol from a carbohydrate source including:

reacting, in a reactor, at a temperature in the range from equal to or more than 170° C. to equal to or less than 270° C., at least a portion of a carbohydrate source in the presence of hydrogen, a solvent, and a catalyst system, to yield ethylene glycol;

and, maintaining the ethylene glycol selectivity within a range of equal to or more than 35% to equal to or less than 85% by continuously or periodically adding additional heterogeneous catalyst to the reactor, wherein the ethylene glycol selectivity is continuously or periodically determined and compared with a one or more pre-set thresholds and wherein additional heterogeneous catalyst is provided to the reactor when such a threshold is reached or exceeded, and wherein the catalyst system is a catalyst system including:

a) a homogeneous catalyst, that is residing in the reactor, which homogeneous catalyst contains tungsten;

b) a first heterogeneous catalyst, that is residing in the reactor, which first heterogeneous catalyst contains one or more transition metals from groups 8, 9 and 10 of the Periodic Table of the Elements supported on a carrier, and which first heterogeneous catalyst further contains an amount of tungsten; and c) a second heterogeneous catalyst, that is continuously or periodically provided to the reactor, which second heterogeneous catalyst contains one or more transition metals from groups 8, 9 and 10 of the Periodic Table of the Elements supported on a carrier, and which second heterogeneous catalyst contains no tungsten; or an amount of tungsten in a molar ratio of moles tungsten to moles transition metal that is less than the molar ratio of moles tungsten to moles transition metal of the first heterogeneous catalyst; and wherein continuously or periodically the second heterogeneous catalyst is added to the reactor and wherein the selectivity towards ethylene glycol is maintained by continuously or periodically adding the second heterogeneous catalyst to the reactor.

2. The process of claim 1, wherein the second heterogeneous catalyst contains no tungsten; or an amount of tungsten in a molar ratio of moles tungsten to moles transition metal that is less than 10:1.

3. The process according to claim 1, wherein in the reactor tungsten species deposit onto the provided second heterogeneous catalyst and the second heterogeneous catalyst is converted into first heterogeneous catalyst.

4. The process according to claim 3, wherein continuously or periodically a portion of the first heterogeneous catalyst is withdrawn from the reactor.

5. The process according to claim 1, wherein further a carbohydrate source is continuously or periodically added to the reactor and wherein the weight ratio of continuously or periodically provided second heterogeneous catalyst to continuously or periodically added carbohydrate source is constantly kept within a range from 0.5:100 to 1.0:100.

6. The process according to claim 1, wherein the first heterogeneous catalyst and/or the second heterogeneous catalyst comprise one or more tungstate compounds selected from the group consisting of tungsten dioxide, tungsten trioxide and combination thereof, deposited onto the transitional metal and/or the carrier.

7. The process according to claim 1, wherein the reactor is a continuously stirred tank reactor.

* * * * *